(12) United States Patent
Chowdhury

(10) Patent No.: US 9,149,495 B2
(45) Date of Patent: Oct. 6, 2015

(54) AMPHIPHILIC NANOTUBES AND MICELLES AND METHOD OF DELIVERY OF BIOLOGICALLY ACTIVE AGENTS

(75) Inventor: Dewan Fazlul Hoque Chowdhury, Loughborough (GB)

(73) Assignee: Neumara Pharma Ltd., Loughborough (GB)

(*) Notice: Subject to any disclaimer, the term of this patent is extended or adjusted under 35 U.S.C. 154(b) by 1673 days.

(21) Appl. No.: 12/102,342

(22) Filed: Apr. 14, 2008

(65) Prior Publication Data
US 2008/0241123 A1    Oct. 2, 2008

Related U.S. Application Data

(63) Continuation of application No. PCT/GB2006/003831, filed on Oct. 16, 2006.

(51) Int. Cl.
*A61K 9/14* (2006.01)
*A61K 33/44* (2006.01)
*A61K 9/107* (2006.01)
*A61K 33/00* (2006.01)
*A61K 41/00* (2006.01)
*A61K 49/18* (2006.01)
*B82Y 5/00* (2011.01)
*B82Y 30/00* (2011.01)
*B82Y 40/00* (2011.01)
(Continued)

(52) U.S. Cl.
CPC ................ *A61K 33/44* (2013.01); *A61K 9/1075* (2013.01); *A61K 9/14* (2013.01); *A61K 33/00* (2013.01); *A61K 41/00* (2013.01); *A61K 41/0052* (2013.01); *A61K 49/1806* (2013.01); *B82Y 5/00* (2013.01); *B82Y 30/00* (2013.01); *B82Y 40/00* (2013.01); *C01B 31/0273* (2013.01); *A61K 9/5094* (2013.01); *Y10T 428/2918* (2013.01)

(58) Field of Classification Search
CPC ................ B82Y 5/00; A61K 9/1694
See application file for complete search history.

(56) References Cited

U.S. PATENT DOCUMENTS

2005/0164169 A1    7/2005    Malak

FOREIGN PATENT DOCUMENTS

WO    WO 03/006043 A1    1/2003
WO    WO 03/060941 A2    7/2003
(Continued)

OTHER PUBLICATIONS

Sano et al., Self-organization of PEO—graft-Single-Walled Carbon Nanotubes in Solutions and Langmuir—Blodgett Films, published paper, Aug. 21, 2001, 4 pages, pp. 5125-5128, vol. 17, No. 17.
(Continued)

*Primary Examiner* — Carlos Azpuru
(74) *Attorney, Agent, or Firm* — McCracken & Gillen LLC

(57) ABSTRACT

A micelle formable from at least one nanotube in a process of self-assembly, the nanotube comprising an amphophilic nanotube (2, 8, 14) made from one or more species selected from the group of carbon, silicon, a noble metal, silicon dioxide and titanium dioxide. A part of the nanotube (2, 8, 14) is functionalised and a surfactant molecule or emulsifying agent is attached to the functionalised part. The nanotube (2, 8, 14) may have magnetic properties. A therapeutic agent may be incorporated in the micelle. The micelle may be coated to form a capsule (24). The capsule (24) can be introduced to the human or animal body for treatment of tumors or targeted drug delivery when a magnetic field or near-IR radiation is applied.

6 Claims, 2 Drawing Sheets

(51) Int. Cl.
*C01B 31/02* (2006.01)
*A61K 9/50* (2006.01)

(56) References Cited

FOREIGN PATENT DOCUMENTS

| WO | WO 03/068185 A1 | 8/2003 |
|---|---|---|
| WO | WO 03/090255 A2 | 10/2003 |
| WO | WO 2004/003561 A1 | 1/2004 |
| WO | WO 2004/046167 A2 | 6/2004 |
| WO | WO 2005/037711 A1 | 4/2005 |
| WO | WO 2005/059508 A2 | 6/2005 |
| WO | WO 2005/069750 * | 8/2005 |
| WO | WO 2005/069750 A2 | 8/2005 |

OTHER PUBLICATIONS

Shin Hye-In et al., Amphiphilic Block Copolymer Micelles: New Dispersant for Single Wall Carbon Nanotubes, published paper, 6 pages, pp. 1451-1456, vol. 26.

Limin Huang et al., Self-organizing high-density single-walled carbon nanotube arrays from surfactant suspensions, published paper, Aug. 23, 2004, 5 pages, pp. 1450-1454, vol. 15.

* cited by examiner

AMPHIPHILIC NANOTUBES AND MICELLES AND METHOD OF DELIVERY OF BIOLOGICALLY ACTIVE AGENTS

CROSS-REFERENCE TO RELATED PATENT APPLICATIONS

This patent application is a continuation of pending PCT Application No. PCT/GB2006/003831, filed Oct. 16, 2006, which designated the United States and claims the benefit of Great Britain Application No. 0520902.8, filed Oct. 14, 2005 and Great Britain Application No. 0612701.3, filed Jun. 27, 2006, which claims the benefit of Great Britain Application No. 0520902.8, filed Oct. 14, 2005, the entire teachings and disclosure of which are incorporated herein by reference thereto.

FIELD OF THE INVENTION

The present invention relates to nanotubes and micelles, and in particular to micelles that are formed from nanotubes and have medical applications.

BACKGROUND

A micelle is an aggregate of surfactant molecules (typically organic molecules that are amphiphilic, meaning that they have a hydrophobic or lipophobic end and a hydrophilic or lipophilic end) dispersed in a liquid colloid. Micelles are often spherical or globular in shape, but can adopt other shapes such as shells, vesicles, clusters, bi-layers, cylinders and ellipsoids.

Micelle formation is affected by several factors. However, micelles will only form by themselves in a process of self-assembly when the concentration of the surfactant is greater than a minimum limit known as the critical micelle concentration (CMC). The CMC can be measured by known phase-change monitoring techniques such as absorption or scattering of radiation.

Nanotubes can be defined generally as substantially tubular structures with a diameter on the nanoscale, for example less than 100 nm. They are typically made from atomic carbon bonded in a $sp^2$ structure, although they have been made from other species. The present invention can include single- and multi-walled nanotubes, coated nanotubes, nanotubes that are open-ended and nanotubes that have one or both of their ends closed.

It is known to functionalise nanotubes and attach drug molecules to the nanotubes for use in drug delivery in the human body. However, the area of functionalisation is not controlled, resulting in a variety of nanotubes with molecules attached in random locations. These nanotubes cannot form micelles.

BRIEF SUMMARY OF THE INVENTION

Embodiments of the present invention provide a micelle formable from at least one nanotube in a process of self-assembly, the nanotube comprising an amphiphilic nanotube made from one or more species selected from the group of carbon, silicon, a noble metal, silicon dioxide and titanium dioxide. Preferably the micelle formed is uniform, i.e. has at least one plane of symmetry.

Further preferred embodiments are claimed in claims 2-13.

The amphiphilic nanotube may be made by covering a functionisable part of one or more of the nanotubes with a coating that includes a hydrophilic or hydrophobic surfactant or emulsifying agent, or with a coating that includes a lipophilic or lipophobic surfactant or emulsifying agent, for example. The coating can be applied to an end, to an extending portion which extends away from an end portion towards a distal end of the nanotube, or to a side of the nanotube such as a hemicylindrical portion of the nanotube surface. The other end or side can be left without a coating, or a coating with opposite hydrophobic or hydrophilic properties can be applied. For example, a hydrophobic coating can be applied to one side of each nanotube and the other side of each nanotube can be left uncoated. Alternatively, a hydrophobic coating can be applied to one end of each nanotube and a hydrophilic coating can be applied to the other end of each nanotube. A first coated part of the nanotube may form a core of the micelle and a second part may form a corona of the micelle, or vice versa.

Examples of suitable surfactant and emulsifying agents for use in the coatings would include nonionic block copolymers such as polyoxypropylene (POP) or polyoxyethylene (POE), ionic block copolymers, polyoxyethelyne glycol (PEG), lipids such as lecithin, diacyllipids such as phosphatidylethanolamine (PE) and poloxemers such as Pluronic® F127. Alternatively, they may be a combination of these and/or other surfactants.

The properties of the liquid colloid will determine the orientation of the nanotubes in the micelle. For example, if the liquid colloid is water then the ends of the nanotubes that are hydrophobic will cluster together at a core of the micelle and the ends of the nanotubes that are hydrophilic will form a corona that defines an outer region of the micelle.

A micelle can also be formed by relying on steric hindrance where one or more (and preferably all) of the nanotubes are provided with a long chain of molecules such as a polymer, e.g. a block copolymer. The block copolymer restricts the spatial arrangement of the nanotubes to the extent that they will form a micelle if the concentration of the nanotubes is greater than the critical micelle concentration (CMC). In this case, the ends of the nanotubes that are not provided with the block copolymer are forced by the steric hindrance to cluster together at a core of the micelle and the ends of the nanotubes that are provided with the block copolymer are forced by the steric hindrance to form a corona that defines an outer region of the micelle.

In some instances, it might be preferable to form a micelle from a variety of different nanotubes.

The nanotube is made of one of silicon dioxide, titanium dioxide, carbon, silicon, a noble metal, or a composite of these materials. Preferably, it is made from carbon, silicon or a noble metal. The noble metal may be titanium, palladium, gold or silver. Preferably the nanotube is made by a manufacturing process rather than produced by a natural process, or supramolecular tubes, or from peptides. The nanotubes may be single walled or multi-walled.

A therapeutic composition or agent (such as a form of pharmaceutical preparation, for example) can be located in the micelle, for example, at the core of the micelle such that it is substantially surrounded or encapsulated by the nanotubes. Alternatively, the therapeutic agent may be in the corona of the micelle, or between the core of the micelle and the corona. The closer the therapeutic agent is to the outside, the easier it is for it to impart its therapeutic benefit without the kinetics being limited to the controlled degradation of the micelle or a coating of the micelle.

Alternatively, the core may remain liquid and a biomarker molecule may be ligated to a magnetic micelle for use in a method of imaging, which may form part of a method of diagnosis. For example, the biomarker may be an antibody marker or a biomarker which interacts with specific cells. The method of diagnosis may be performed on cells in vivo or in vitro.

The micelle can be coated with a coating that encapsulates the plurality of nanotubes to form a nanotube-micelle capsule. This can be achieved by processing the micelle by drying or removing the liquid colloid and then spraying or coating the micelles using lipids, pharmaceutical polymeric materials or the like in order to form a semi-rigid or rigid nanotube-micelle capsule. Preferably, the coating is applied directly through layer by layer electrostatic deposition in solution without removing the solvent. The nanotube-micelle capsules can be suspended in a suitable liquid and injected or otherwise introduced into a human or animal body for therapeutic purposes.

A portion, or all, of the nanotube can be magnetic, possessing one or more of diamagnetic, paramagnetic and ferromagnetic properties. The nanotubes can be doped, coated with magnetic materials or grown to have magnetic properties for example. The doping or coating can take place before or after the formation of the micelle. Alternatively, attachment of a 'magnetising' element may be undertaken during or after micelle formation.

Additional layers of surfactant can be added around the micelle to enhance stability through electrostatic interaction or steric hindrance. The magnetic properties of the micelle can be improved by adding magnetic particles within the additional surfactant layers as a non-bonded dispersion or by binding magnetic particles to the nanotubes or additional surfactant layers.

Both, nanotube-micelle capsules and non-coated micelles after being introduced into a human or animal body, can be made to vibrate in response to a magnetic field. This will have the effect of locally raising the temperature within the body and can be used to destroy tumour cells via tumour ablation therapy. Such vibrations can also be used to disrupt the micelle or coating for the targeted delivery of the therapeutic composition or agent at the core of the micelle. Delivery can also be triggered by other means such as a near-IR radiation.

At least one of the nanotube micelles and nanotube micelle capsules may be introduced to the body in various ways including direct injection, ingestion, inhalation or topical administration. They may be directed to a target within the body via the body's natural pathways, for example when the capsule or micelle has been ligated to a marker molecule, or via the magnetic properties of the nanotube or micelle.

A beam of radiation, such as near-infra red (IR) radiation, may be directed at the afflicted part of the body. The nanotubes will absorb some of this radiation and vibrate, locally raising the temperature. The locally raised temperature may affect the body, for example by denaturing the tumour cell. Alternatively, the increased thermal energy may cause the coating of the capsule to breakdown, either gradually or suddenly, and thereby release the therapeutic agent having delivered it to the desired location This method of treatment is particularly suitable when the nanotubes are made of carbon.

Alternatively, an alternating magnetic field of a resonant frequency can be applied to the part of the body. If the nanotubes are magnetic, or the micelles have embedded magnetic particles then the micelles will vibrate in response, generating thermal energy as described above, with similar effects.

Although the invention is intended for use in medical applications, its application is broader and the nanotube micelles may be incorporated in composite polymers or electropolymers to enhance material properties such as conductivity and toughness. The nanotube micelles may also find use in optics, for example as nano-emissive devices in field emission displays, where the nanotube micelles can be bound to suitable substrates.

The invention also provides methods of manufacturing nanotubes as claimed in claims 14 to 18.

The invention also provides methods of treatment using the micelles according the invention, as claimed in claims 19 to 22.

Other aspects, objectives and advantages of the invention will become more apparent from the detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE DRAWINGS

Figure 1:
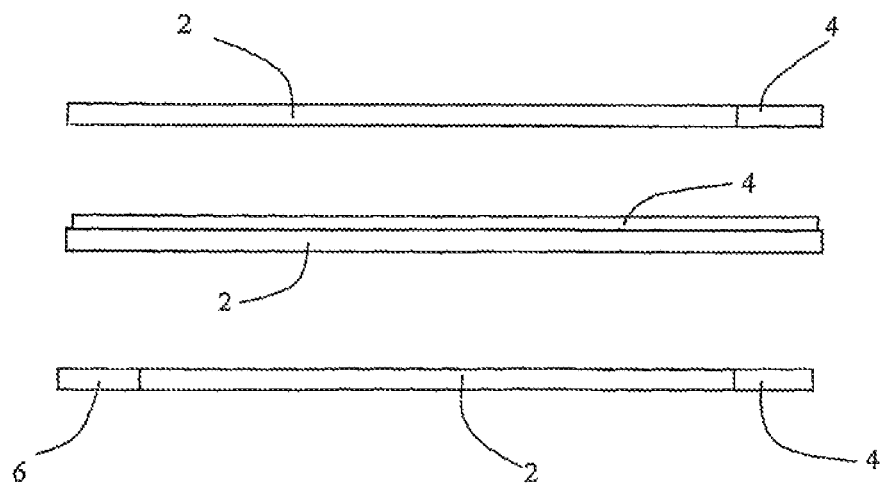
FIG. 1 is a schematic drawing of three different amphiphilic nanotubes that can be used to form a micelle according to the present invention.

With reference to FIG. 1, a single-walled carbon nanotube 2 can be coated at one end or side with a hydrophilic surfactant coating 4. The other end or side can be left uncoated (as in the case of the first and second nanotubes) or coated with a hydrophobic surfactant coating 6.

The nanotubes 2 may be formed by one of the following methods:

Side Wall Functionalisation Via Magnetic Alignment

Nanotubes with magnetic properties are aligned and anchored to a substrate (such as a metal plate or container, for example) by applying a magnetic field. The nanotubes may be aligned in a monolayer, such that the side of the nanotubes in contact with the container surface is not available for binding with the surfactant. The nanotubes are then treated with surfactant solution at exposed regions with subsequent attachment of surfactant molecules. Upon washing off the excess surfactant solution the tubes can be released from the container surface by removal of the magnetic field used to hold the nanotubes in a specific conformation during the surfactant coating stage.

Side Wall Functionalisation Via Electrical Alignment

One of the most common processes used to produce nanotubes leads to tubes which have catalyst ions at one or both ends of the nanotubes. Such nanotubes can be aligned in an electrochemical cell between the anode and cathode, with the end containing the catalyst ions being attracted to the cathode. The nanotubes can be aligned in a layer, which is preferably a monolayer, across a cathode substrate. A protective material, e.g. a polymer, can be used to coat the exposed surface.

Then the nanotubes can be released from the substrate. The uncoated surface can then be functionalised via treatment with a weak acid. Subsequently a surfactant molecule can be attached to the functionalised surface.

Filling of Open Nanotubes

In the case where the nanotubes are open at one end and closed at the other end, the nanotubes can be treated with a suitable solvent, such as a surfactant solvent, to reduce interfacial tension. The nanotube in the solvent is placed in a vacuum chamber so that the solvent is received in the open end of the nanotubes. The nanotubes are then washed to remove excess solvent. A suitable molecule in solution is added to the filled but previously empty nanotubes. The molecule will undergo bonding with surface of the solvent contained in the nanotube in preference to bonding with the surface of the nanotube. For example, the solvent may be a surfactant and the molecule may be obtained from an emulsifier solution.

Functionalisation of a Closed End of a Nanotube

Nanotubes generally have ends that are more susceptible to oxidation than the other parts of the tube, for example in the presence of a weak acid, ozone or oxygen. Thus, in the case where a nanotube has an open end and a closed end, the closed end can be functionalised by washing the nanotube with a weak acid. A suitable molecule, e.g. a surfactant molecule, can then be attached to the functionalised end. If both ends of the nanotube are closed, then the dilute acid wash can be optimised so that only one end is functionalised.

Figure 2:
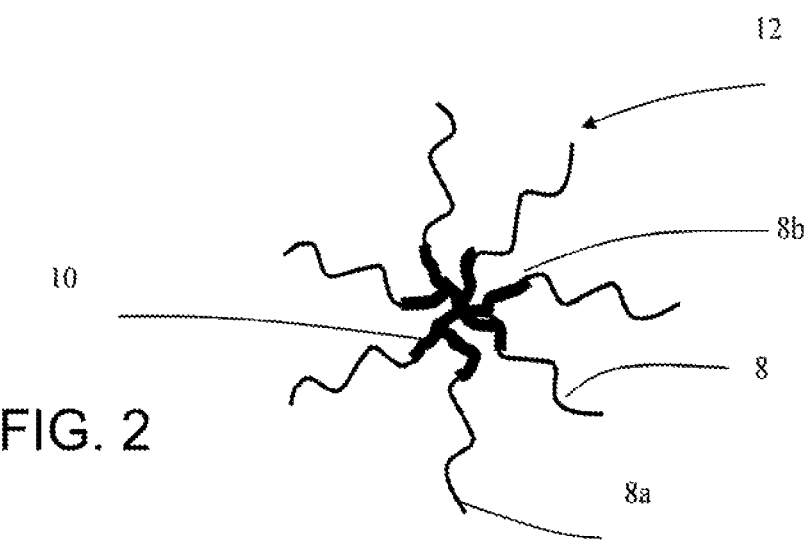
FIG. 2 is a schematic cross-section drawing of a spherical micelle according to the present invention.

If the concentration of nanotubes 2 in a liquid colloid is greater than the critical micelle concentration (CMC), then, the nanotubes will spontaneously form a micelle due to the amphiphilic nature of the surfactant coated nanotubes. This occurs to reduce the surface free energy of the system. An example of a spherical micelle where the liquid colloid is water is shown in FIG. 2. In this case, each nanotube 8 has a hydrophilic end 8a and a hydrophobic end 8b. The hydrophobic ends 8b of the nanotubes 8 cluster together at the centre of the micelle to form a core 10 while the hydrophilic ends 8a point away from the centre of the micelle to form a corona 12 that is substantially spherical. As the micelles form, the nanotubes can solubilize therapeutic agents through encapsulation of the continuous phase media within the micelle, and preferably within the core.

Figure 3:
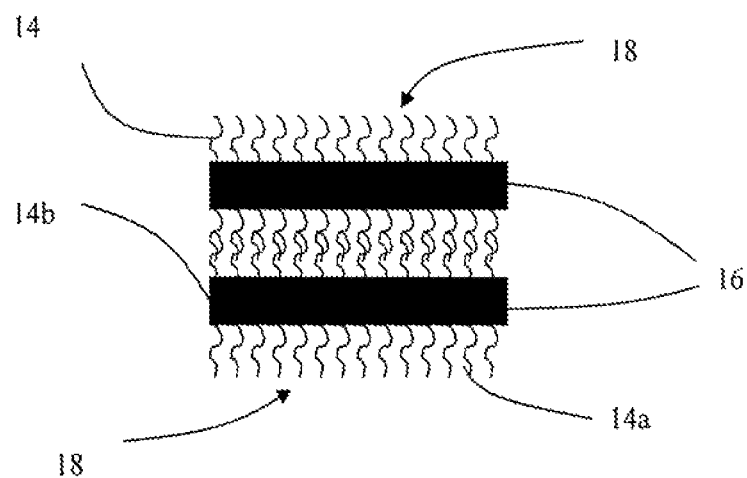
FIG. 3 is schematic cross-section drawing of a bi-layer micelle according to the present invention.

An example of a bi-layer micelle where the liquid colloid is water is shown in FIG. 3. In this case, each nanotube 14 has a hydrophilic end 14a and a hydrophobic end 14b. The hydrophobic ends 14b of the nanotubes 14 cluster together to form a pair of elongate cores 16 while the hydrophilic ends 14a point away from the respective cores (in the case of the nanotubes located between the cores this means that the hydrophilic ends may point towards the other core) to form a corona 18 that is substantially cylindrical.

Figure 4:
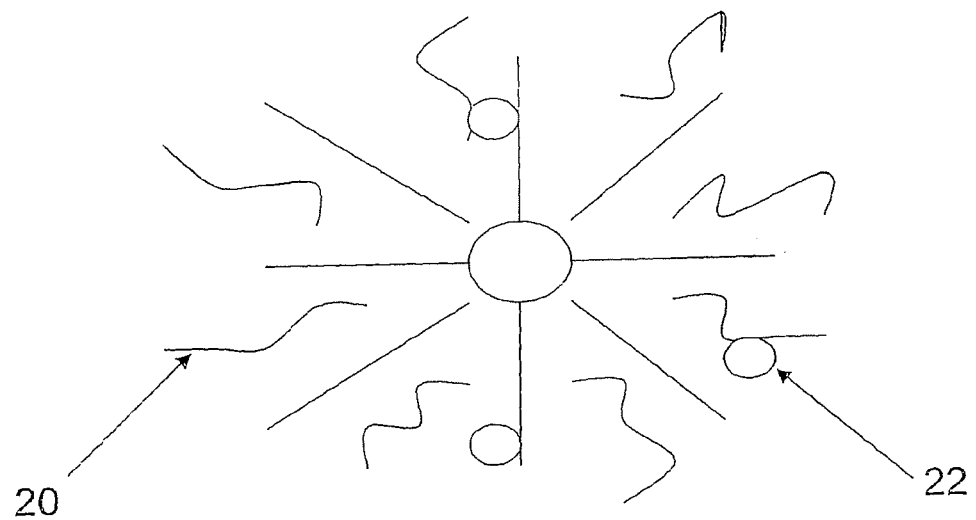
FIG. 4 is a schematic cross-section drawing of a spherical micelle with additional surfactant layers.

Electrostatic repulsion between the hydrophobic or hydrophilic outer head groups on the surfactant coated micelle leads to a uniform micellar structure. However, one or more additional layers of different types of surfactant molecules 20 may be added as shown in FIG. 4. The additional surfactant molecules 20 may enhance the stability of the micelle through electrostatic interaction or via steric hindrance by virtue of the size and long chain length of the surfactant molecules 20. The external surfactant layer(s) can be such that micelle formation occurs upon reaching the threshold concentration of the surfactant coated nanotubes where the continuous phase is oil, thus forming a type of emulsified micellar suspension. Further magnetization may be imparted by adding magnetic or metallic particles 22 of various shapes in various places, including within the additional surfactant layers, as a non-bonded dispersion amongst the long chains of the surfactant molecules 20, and by addition of metal particles 22 which bind with the individual surfactant-coated nanotubes 2.

Figure 5:
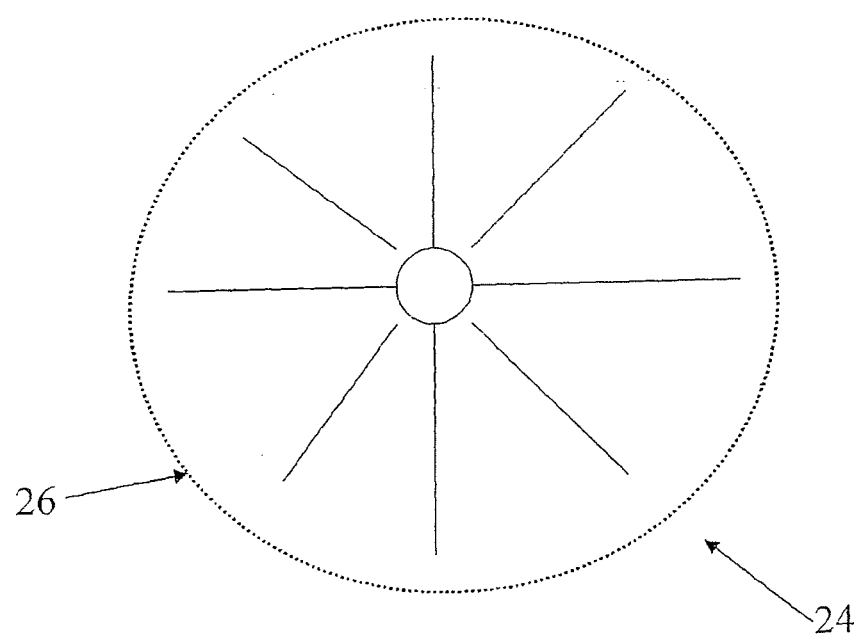
FIG. 5 is a schematic cross-section drawing of a spherical micelle with an outer coating.

FIG. 5 shows a nanotube-micelle capsule 24 which has been made by further processing a nanotube micelle to encapsulate it within an outer coating 26. The coating 26 is made of a biocompatible material, for example a lipid or a pharmaceutical polymeric material. The material and structure of the outer coating 26 is chosen for its intended purpose and may resist degradation in the body, or may be designed to degrade over time so as to give a controlled release of the nanotube-micelle and optionally the therapeutic agent.

The coating 26 completely encapsulates the nanotube micelle, and is substantially rigid so that it constrains the movement of the nanotubes inside.

The nanotube-micelle capsule 24 may be made in a variety of ways. Optionally the first step of in making the capsule 24 is removal of solvent from the nanotube micelle. The nanotube micelles are substantially rigid and can be coated using various methods to make the rigid nanotube-micelle capsule 24. This may be by spray coating, vapour deposition, or electrostatic layer by layer deposition. The nanotube-micelle capsule 24 can then be re-suspended in aqueous media and ligated to a marker molecule and its therapeutic application may include either direct administration by injection, into tumor sites, or systemic administration by injection, followed by the use of a magnetic field, to ablate tumor cells.

Because the nanotubes are spatially restrained within the coating 26 of the nanotube-micelle capsule 24, applying a magnetic field or near-IR radiation results in a vibratory excitation of the nanotube micelles and any particles 22 within the nanotube capsule 24. This results in a higher localized temperature than that which might be achieved by using individual nanotubes, thus making it a more efficient mode of tumor ablation therapy.

The coating 26 may be broken down by the vibrations or the thermal energy to release the therapeutic agent from the nanotube capsule 24.

In the case where the nanotube micelle or nanotube-micelle capsule 24 is intended for use in the human or animal body, the size of the micelle is necessarily limited. The size of the nanotube micelle is controlled primarily by the length of the nanotubes. The nanotube length can be reduced prior to or after functionalisation through various methods, e.g. ultra homogenisation or grinding between plates. Preferably, the method involves oxidising both ends of the nanotubes, adding a surfactant to the nanotubes to bond with the ends, then homongenising or grinding between plates to break the nanotubes into pieces. The resulting nanotubes have surfactant at just one end.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nanotube characterized by being amphiphilic, whereby a plurality of the nanotubes are capable of self-assembly to form a micelle.

2. A nanotube according to claim 1 made from one or more species selected from the group consisting of carbon, silicon, and a noble metal.

3. A nanotube according to claim 1, wherein the nanotube comprises a functionalised part, to which is attached a species selected from the group consisting of a surfactant, an emulsifying agent and a polymer.

4. A nanotube according to claim 3, wherein the functionalised part is an end of the nanotube.

5. A nanotube according to claim 3, wherein the functionalised part is a substantially hemicylindrical surface portion of the nanotube.

6. A nanotube according to claim 1, wherein at least a portion of the nanotube is magnetic.

* * * * *

UNITED STATES PATENT AND TRADEMARK OFFICE
CERTIFICATE OF CORRECTION

PATENT NO. : 9,149,495 B2  
APPLICATION NO. : 12/102342  
DATED : October 6, 2015  
INVENTOR(S) : Dewan Fazlul Hoque Chowdhury Page 1 of 1

It is certified that error appears in the above-identified patent and that said Letters Patent is hereby corrected as shown below:

Title page, "item (75)" should read -- item (76) --

Title page, item (73), please delete, "Assignee: Neumara Pharma Ltd."

Signed and Sealed this  
Ninth Day of February, 2016

Michelle K. Lee  
*Director of the United States Patent and Trademark Office*